United States Patent [19]

Kellner

[11] Patent Number: 4,504,365

[45] Date of Patent: Mar. 12, 1985

[54] NON-DESTRUCTIVE CATHODIC DISBONDMENT TESTING OF PIPEWRAP COATINGS

[75] Inventor: Jordan D. Kellner, Wayland, Mass.

[73] Assignee: The Kendall Company, Boston, Mass.

[21] Appl. No.: 438,106

[22] Filed: Nov. 1, 1982

[51] Int. Cl.³ ..................... G01N 27/30; G01N 27/46
[52] U.S. Cl. ................................. 204/1 T; 204/147;
436/6; 204/196
[58] Field of Search ............... 204/1 T, 1 C, 147, 196,
204/400, 401, 404; 324/360, 362, 456, 51, 54, 71
E; 73/86

[56] References Cited

U.S. PATENT DOCUMENTS 4,095,176  6/1978  Maes et al. ..................... 324/65 CR
4,130,464 12/1978  Kanno et al. ....................... 204/1 T

OTHER PUBLICATIONS

A. J. Bard et al., "Electrochemical Methods", Wiley (1980), pp. 10–11 and 136–137.
"Electrochemical Techniques for Corrosion", National Association of Corrosion Engineers (1977), pp. 61–65, J. H. Payer Electrochemical Methods for Coatings Study & Evaluation.
L. F. G. Williams, "Automatic Corrosion Rate Monitoring of Metals in Solution," *J. Electrochem. Soc.*, vol. 127, pp. 1706–1709 (1980).

*Primary Examiner*—Aaron Weisstuch
*Attorney, Agent, or Firm*—Frederick R. Cantor

[57] ABSTRACT

A method and apparatus herein is disclosed that consists of establishing and equilibrating a circuit path through a working test pipe electrode and a counter electrode in an electrolyte fluid in which said test pipe electrode achieves a state of cathodic protection. Disconnecting said cathodically protected working test pipe electrode from said counter electrode. Then re-establishing a circuit path through said working test pipe electrode, said counter electrode, and a reference electrode, in said electrolyte fluid along with an electronic control and measuring means. Subsequently causing a measured known voltage step to be applied to said working test pipe electrode. Then measuring the current flowing after application of said measured applied voltage step. Finally, then analyzing said current flow data and thereby determining the double layer capacitance at the interface between said working test pipe electrode and said electrolyte fluid as a measure of disbonded area thereon.

8 Claims, 7 Drawing Figures

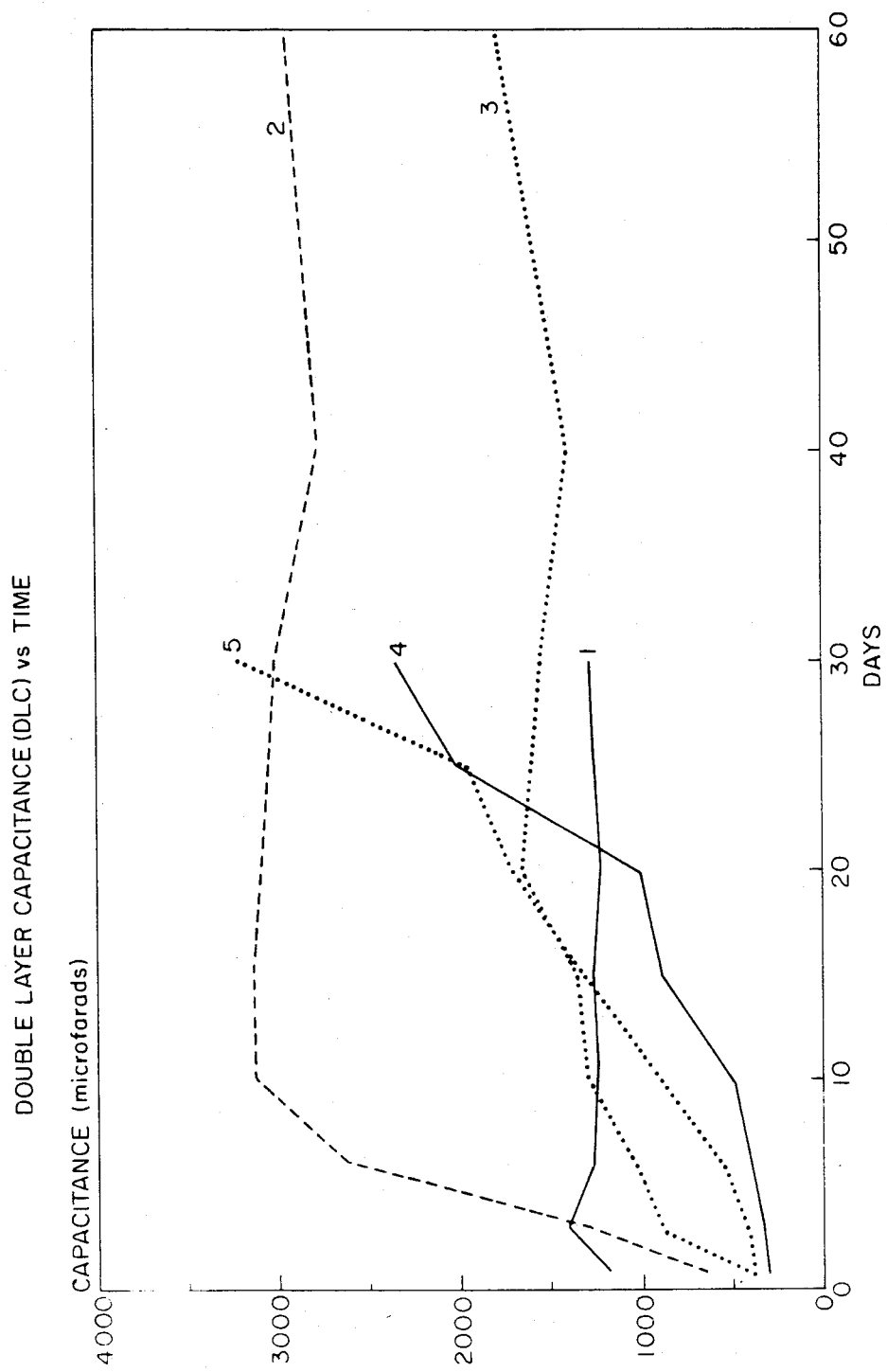

NON-DESTRUCTIVE CATHODIC DISBONDMENT TESTING OF PIPEWRAP COATINGS

BACKGROUND OF THE INVENTION

The present invention relates to methods of and apparatus for the evaluation of corrosion protection afforded to a metallic surface by a protective surface coating thereon.

The present invention relates more specifically to a method of and apparatus for the measurement of the extent of cathodic disbondment of an anti-corrosion protective surface layer overlaying a metallic surface, such as in a metal pipeline, or the like.

There exists at the present time a need for a method of and an apparatus for the non-destructive measurement of the extent of cathodic disbondment of an adherent anti-corrosion protective coating from its associated pipeline outer surface.

Metallic surfaces are adversely affected by numerous corrosive electrolytic fluids that contact these surfaces. In the natural gas and petroleum industries, e.g., corrosion occurs extensively on the outer surface of both implanted and above-ground pipelines.

In order to reduce, or entirely eliminate this undesirable metallic surface corrosion, anti-corrosion protective coatings are extensively used in the pipeline industry. These ubiquitous anti-corrosion protective coatings frequently take the form of a helically-applied tape-like protective outerwrapping. The tape-like protective component may be applied directly over an unprepared pipeline outer surface, or may, in fact, be overlaid onto a primer-coated, pretreated pipeline outer surface.

An important measurable parameter directly relating to the performance of anti-corrosion pipeline protective coatings is that of cathodic disbondment. This property is defined as the extent to which an anti-corrosion protective coating overlaying a metallic surface will disbond as a result of a cathodic reaction, around an unintentionally-induced holiday, or discontinuity, in the protective coating, in a case where the pipe has been subjected to cathodic protection potentials in the soil environment.

Cathodic protection as it is used here, refers to the phenomenon of applying a small potential to a metallic pipeline that is buried in the ground. This imparted cathodic status of the buried pipeline will tend to limit or protect against corrosion attacking the metal surface.

The prior art methods that have been used heretofore by the industry to measure the property of cathodic disbondment is the ASTM/G-8 ("Cathodic Disbonding of Pipeline Coatings") in the United States, and DIN 30-670, a similar method employed throughout Europe.

The prior art methods describe accelerated procedures for the determination of the cathodically disbonded area by means of exposure of the test pipe segment with its adherent anti-corrosion protective coating to a salt electrolyte solution, for a period of from 30 to 90 days, following the cutting of the protective coating in the form of an intentionally-induced holiday, and with a potential being applied to the system.

Following the testing period, the anti-corrosion protective coating is then cut at the intentionally-induced holiday, carefully peeled back from the induced holiday, until resistance is felt, and the extent of the disbonded area is then physically measured.

Some of the major disadvantages of the existing prior art cathodic disbondment measuring methods are the following:

The methods are physically destructive.

They are subjective in interpretion of results, due to subjectively determining the point at which resistance is met.

They are quite time-consuming, requiring longer time periods to complete each test.

The present invention has elegantly circumvented the above-described disadvantages of the prior art methods, and some of its important features are the following:

The present method is non-destructive, the electrical measurements being performed in situ.

The instant method utilizes recordable electrical measurements, and therefore, is not biased by the subjective interpretations of the operator that are required in the prior art methods.

Information relating to the extent of the cathodically disbonded area, may be obtained on a daily basis, rather than at the conclusion of the prior art's 30 to 90 day testing periods.

The electrical measurements of the present invention are readily amenable to computer storage, manipulation and retrieval of test data.

Finally, the present invention method requires the use of considerably smaller amounts of pipe material than in the prior art method.

SUMMARY OF THE INVENTION

It is, therefore, an object of the present invention to provide a method of and an apparatus for the evaluation of corrosion protection afforded to a metallic surface by an anti-corrosion protective coating thereon.

It is a further object of the present invention to provide a method of and an apparatus for the measurement of the extent of cathodic disbondment of an anti-corrosion protective layer overlaying a metallic surface, such as in a metal pipeline, or the like.

These and other objects of the present invention are accomplished in accordance with the illustrated exemplary embodiment of the instant invention, by a method of and an apparatus for the non-destructive cathodic disbondment testing of pipewrap coatings.

The method here consists of (a) establishing and equilibrating a circuit path through a working test pipe electrode and a counter electrode in said electrolyte fluid in which said test pipe electrode achieves a state of cathodic protection; (b) disconnecting said cathodically protected working test pipe electrode from said counter electrode; (c) re-establishing a circuit path through said working test pipe electrode, said counter electrode, and a reference electrode, in said electrolyte fluid along with an electronic control and measuring means; (d) causing a measured known voltage step to be applied to said working test pipe electrode; (e) measuring the current flowing after application of said measured applied voltage step; and then analyzing said current flow data and thereby determining the double layer capacitance at the interface between said working test pipe electrode and said electrolyte fluid.

BRIEF DESCRIPTION OF THE DRAWINGS

In order that the present invention may be more fully and readily understood, and so that further features thereof may be appreciated, the invention will now be described by way of example with reference to the accompanying drawings, in which like reference characters are used throughout to designate like parts, and in which:

FIG. 6 is a graph chart depicting double layer capacitance as a function of time.

DETAILED DESCRIPTION OF THE PREFERRED EMBODIMENT

Figure 1:
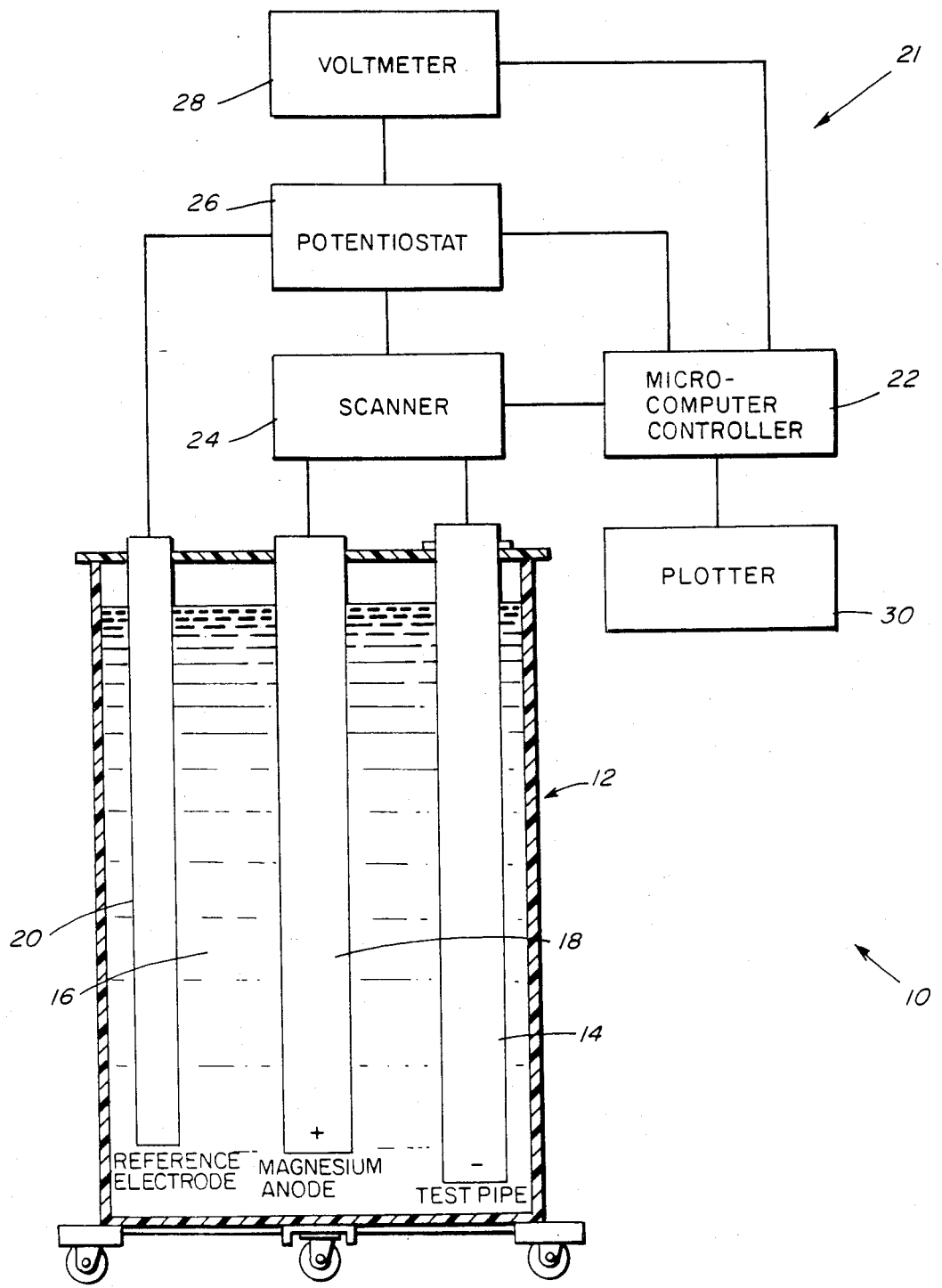
FIG. 1 is a cross-sectional view of an exemplary embodiment of the present invention, also including a block diagram of the electronic control and measuring system employed therewith.

Referring now to FIG. 1, which is a cross-sectional view of an exemplary embodiment of the present invention, also showing a block diagram of the electronic control and measuring systems employed therewith.

The apparatus for carrying out the measurement of the extent of cathodic disbondment is depicted here generally as 10. The apparatus housing 12 is also shown as being essentially a vessel-like structure.

A test pipe working electrode 14, is oriented vertically, and suspended within the housing 12.

An electrolyte solution 16, fills the housing 12, and surrounds the suspended test pipe working electrode 14, as well as a vertically-oriented, and suspended, counter electrode, being a magnesium positive anode 18. A counter electrode of steel composition, with the use of a rectifier, may also be employed.

A reference electrode 20, being a standard calomel reference electrode, is also similarly oriented and suspended in the electrolyte solution 16.

Figure 2:
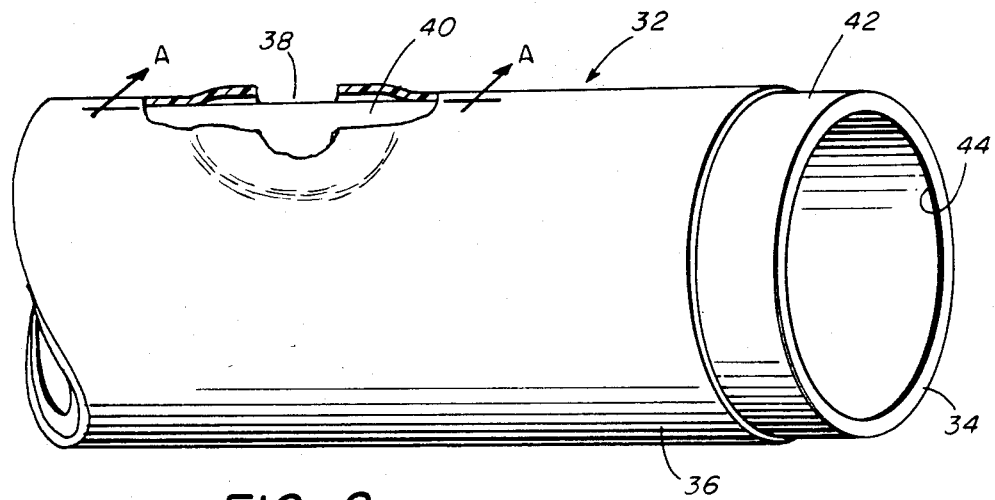
FIG. 2 is a fragmentary perspective view of a test pipe specimen showing a discontinuity or holiday in the protective coating, and an associated area of cathodic disbondment.

FIG. 2 is a fragmentary perspective view of a test pipe specimen showing a discontinuity or holiday, in the protective coating, and an associated area of cathodic disbondment.

A fragment of the test pipe specimen 14, is depicted here generally as 32. Covering the metallic tubular hollow pipe 34, is an anti-corrosion protective coating 36.

A discontinuity, or holiday, here intentionally-induced for testing purposes, in the protective coating 36, is shown here as 38.

The area of cathodic disbondment, being the region of separation, or disbondment, of the protective coating 36 from the adjacent outer pipe surface 42, is depicted here as 40.

The inner pipe surface is shown here as 44.

Figure 3:
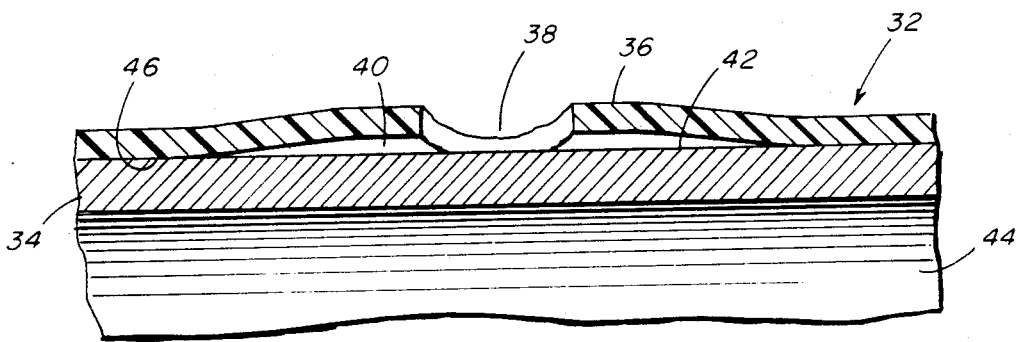
FIG. 3 is an enlarged cross-sectional view of the test pipe specimen of FIG. 2, showing a holiday and an associated area of cathodic disbondment in the protective coating, taken along line A—A of FIG. 2.

FIG. 3 is an enlarged, partial, cross-sectional view of the test pipe specimen of FIG. 2, showing the holiday and the associated area of cathodic disbondment in the protective coating, taken along line A—A of FIG. 2.

The extent of the cathodic disbonded region 40, is more clearly visualized in this view. The electrolyte solution 16 in the apparatus housing 12, infiltrates through the induced holiday 38 and by means of a reaction with the adhesive 46, a separation or disbondment of the anti-corrosion protective coating 36 from the outer pipe surface 42 will occur, resulting in the discrete, well-defined region of cathodic disbondment 40.

The chemical cathodic reaction occurring at the holiday may be characterized as:

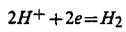

The basic chemical cathodic reaction occurring at the region of cathodic disbondment 40, may be characterized as:

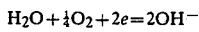

What now follows is a discussion of the electrical theory and background, as well as a discussion of the electrical principles and techniques as employed in the instant invention.

Figure 7:
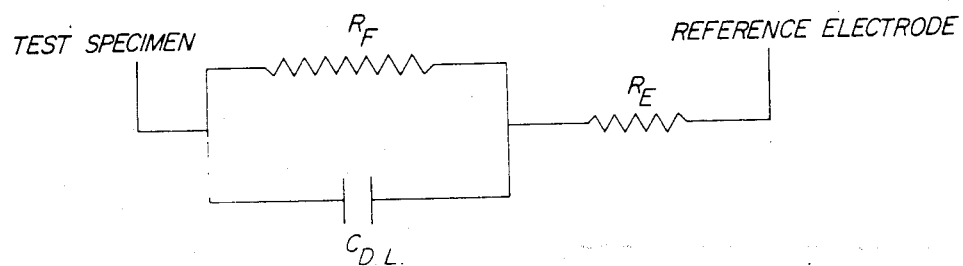
FIG. 7 is a schematic diagram of the equivalent electrical circuit formed when a metal electrode is immersed in an electrolyte solution.

The capacitor formed when a metal electrode is immersed in an electrolyte solution has been studied since its discovery by Helmholtz in the last century. The electrode in contact with the electrolyte can be represented in its transient electrical behavior by the equivalent circuit shown in FIG. 7 where $R_F$ is the faradaic resistance, $R_E$ is the electrolyte resistance, and $C_{D.L.}$ is the capacitance of the double layer. The electrolyte resistance, $R_E$, which includes all resistances between the reference electrode 20 and the test pipe working electrode specimen 14, must be kept to a minimum in order to assure accurate voltage measurement and to eliminate a time lag before the charging current becomes constant. The faradaic resistance, $R_F$, should be high, since this indicates that the faradaic current is low. A correction is made for the faradaic current, however, as described below.

The surface of the metal test pipe electrode 14, acts as one plate of a capacitor, and the electrolyte 16, acts as the other plate. The amount of charge that can be stored by this capacitor, is proportional to the total area of the electrode that is wetted by the electrolyte. This principle has been used to determine the surface areas of porus electrodes.

The single pulse, square wave technique first developed by Hackerman, et al, was used in the instant invention.

The double layer capacitance, $C_{D.L.}$, or DLC, is determined from measurements of the charging current after a potential step is applied, i.e., since by definition the capacitance is:

$$C_{D.L.} = i_C/(dV/dt) \text{ OR } C_{D.L.} = 1/\Delta V \int i_C dt \qquad (1)$$

where t is time in seconds, and V is the potential.

The integration of this equation yields, $$\ln i_C = \ln i_0 - i_0 t/\Delta V C_{D.L.} \qquad (2)$$

where $i_0$ is the initial current. A plot of the log of the current vs. time results in a straight line. The slope of this line, m, is used to calculate the capacitance.

$$C_{D.L.} = -i_0/\Delta V m \qquad (3)$$

The single square wave pulse is imposed on the test pipe working electrode specimen 14 long enough to assure decay of the charging current to zero or some steady value.

The test pipe working electrode specimen 14 is temporarily disconnected from the magnesium anode 18, and the double layer capacitance, $C_{D.L.}$, is then measured by the potential step technique. The test pipe working electrode specimen 14 is then subjected to a voltage step (rise time 0.1 usec) of optimally 100 mv, after which the current decay is monitored with time. Note that a voltage step in the range of from about 30 to 300 mv may be applied to the test pipe electrode. If it is concluded by statistical curve fitting, that the current measured is indeed the double-layer capacitor charging current, then the double-layer capacitance, $C_{D.L.}$, is calculated from the decay curve.

A previously established calibration curve is then used in order to determine the total area of the test pipe specimen electrode 14 that is wetted by the electrolyte. This area has been shown to correspond closely with the region of cathodic disbondment, by the further comparison with the area of cathodic disbondment as measured when using the destructive prior art techniques, such as in ASTM G-8.

All particulars of ASTM G-8 were followed in regard to set-up of the test pipe specimen 14. However, in addition to these, each test pipe specimen 14, was connected electrically to an electronic control and measuring system 21, according to the schematic block diagram shown in FIG. 1.

The electronic control and measuring system 21 of the present invention, consists of a micro-computer controller 22, a scanner 24, a potentiostat 26, a voltmeter 28, and a plotter 30. The scanner 24 is used to allow all test pipe working electrode specimens 14 to be connected to the electronic control and measuring system 21, in succession and automatically, on a daily basis. The microcomputer controller 22, may also be programmed to connect any particular test pipe working electrode specimen 14 to the electronic control and measuring system 21. The potentiostat 26, fixes the voltage between the test pipe specimen working electrode 14, and a reference electrode 20, (standard Calomel reference electrode), allowing a sufficient current to flow between the test pipe working electrode 14, and the counter electrode 18 (magnesium anode).

The voltage applied by the potentiostat 26 is controlled by computer software, since the potentiostat 26, contains an analog to digital converter, and a compatible interface.

The plotter 30 may be used to obtain paper records of the current and voltage output of the test pipe working electrode specimens 14. The voltmeter 28 samples the current to voltage converter of the potentiostat 26 at a rate of 77 readings/sec, and transmits the obtained data to the computer controller 22. The voltmeter 28, scanner 24, plotter 30, and computer controller 22, are all connected with a parallel interface.

Figure 4:
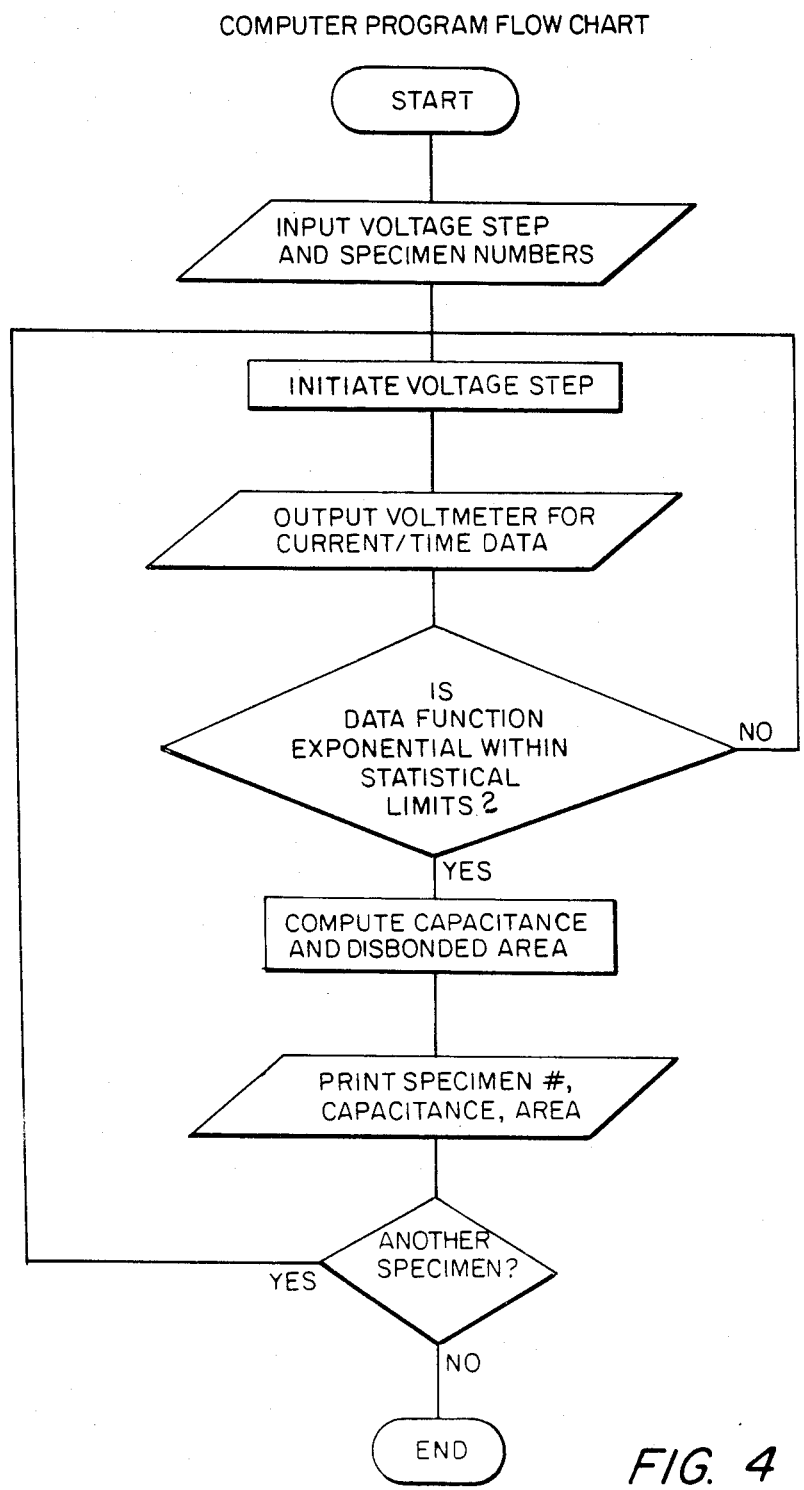
FIG. 4 is a computer program flow chart depicting the steps of the program stored in the computer controller of an exemplary embodiment of the present invention.

FIG. 4 is a computer program flow chart depicting the steps of the program stored in the computer controller of an exemplary embodiment of the present invention.

In the exemplary embodiment of this instant invention, a computer program was developed which was used to direct the electronic measuring and control system 21, shown in FIG. 1. This program allows the user to input the test pipe working electrode specimen 14 desired to be measured, along with the potential step parameters. The current output of the test pipe electrode specimen 14, is also sent to the computer controller 22, for manipulation and statistical testing and curve fitting. The various steps in the present method are indicated in FIG. 4 which shows a flow chart for the program used here and stored in the computer controller 22.

The computer controller 22 prompts the user for input data for the initial and final voltages required for the potential step, as well as the test pipe electrode specimen 14 to be connected through the scanner 24. The test pipe electrode specimens 14 are disconnected from the magnesium anode 18, and allowed to equilibrate for at least 15 minutes prior to their connection to the electronic measuring and control system 21.

In the present method, current measurements are sent to the computer controller 22 from the voltmeter 28 every 14 milliseconds. The regression values for an exponential fit for these data points are calculated by the computer controller 22, and the functional equation is generated. The calculation includes the coefficient of determination, $R^2$, which indicates the quality of fit achieved by the regression, and the F-Ratio. If the F-Ratio indicates a significant exponential relationship at the 95% confidence level, then the data indicate that distributive capacitance effects, and significant faradaic currents are absent. In this case, the data are listed and the program continues into the next step.

The computer-generated current decay curve is of the form:

$$i_C = i_0 EXP(-mt)$$

where the coefficient m is the slope discussed earlier, $i_c$, is the charging current in amperes, $i_o$ is the peak current at $t=o$, and t is the time in seconds. The capacitance in Farads is given by equation 3. The list of capacitances for all test specimens is then printed out.

The following is a discussion of the technique for calculating the cathodically disbonded area. The double layer capacitance (DLC), per unit area of test pipe electrode 14 surface, was measured for uncoated pipe as a function of pipe potential vs. the standard reference calomel electrode.

Figure 5:
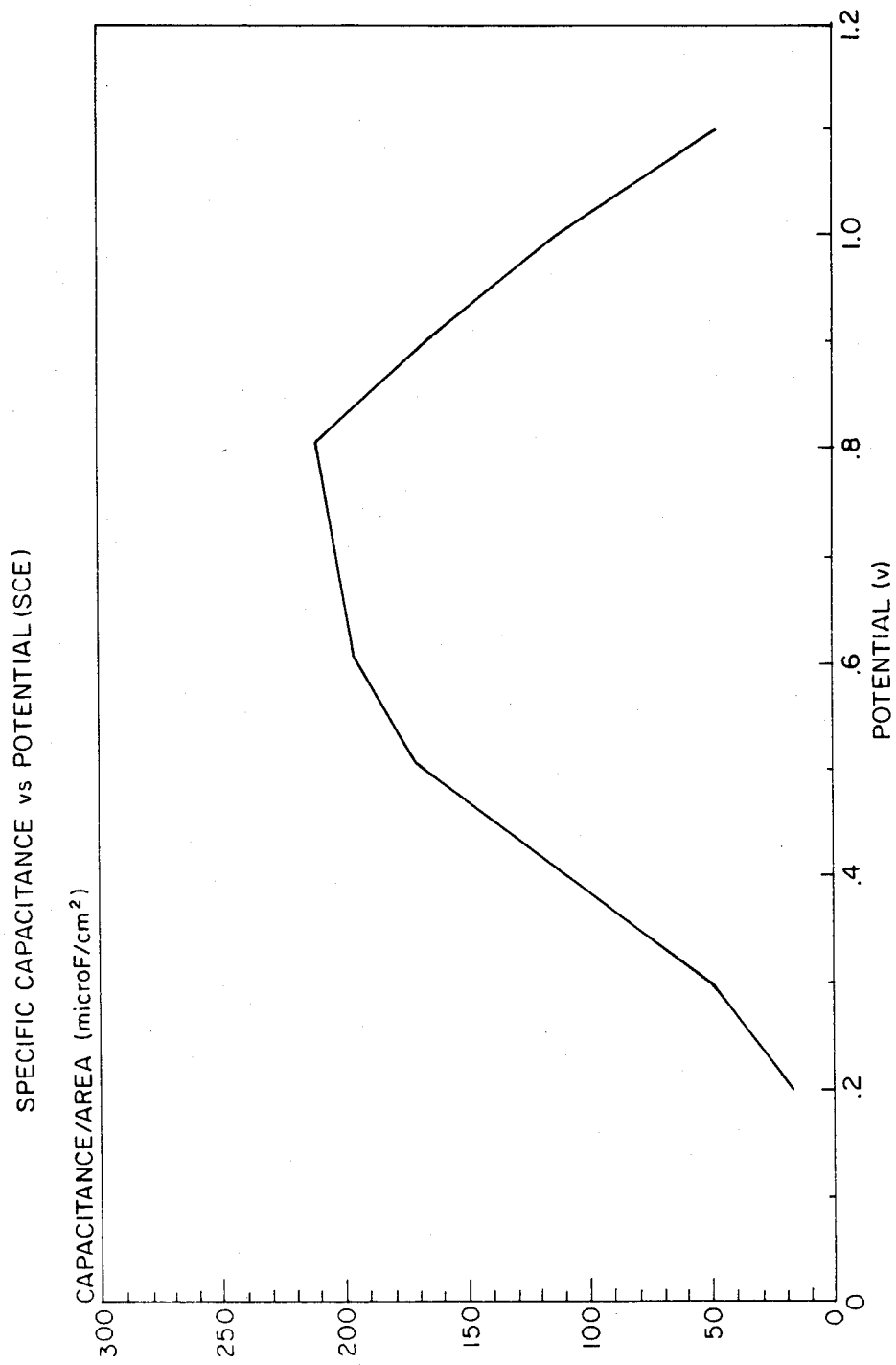
FIG. 5 is a graph chart depicting specific capacitance as a function of various potential values.

FIG. 5 is a graph chart depicting specific capacitance as a function of various potential values.

The data shown in FIG. 5 were used to prepare a calibration curve, in order to calculate the wetted cathodic disbonded area for the test specimens under various potentials. A 100 mv excursion between −0.8 volts and −0.7 volts was adopted for the potential step, in order to utilize a portion of the curve that has a nearly constant specific capacitance.

At these potentials, Faradaic currents are approximately 10% of the charging current for small cathodically disbonded areas. Therefore, the current flowing 0.3 seconds after the voltage pulse was subtracted from the current values. The basic computer program used in this method and depicted in FIG. 4, calculates the regression curve fit, and rejects any data that fails to fit an exponential curve at the 95% confidence level. These precautions assure that only the charging current for the double layer capacitance (DLC) is being measured. The specific capacitance used for the calculations of the cathodic disbonded area was 200 microfarads/cm$^2$.

Table I below lists five representative test pipe samples, with the cathodically disbonded area being determined by both the double layer capacitance (DLC) of the present method, as well as physically by the ASTM G-8 test. The areas of cathodic disbondment given below are for the total of three intentionally-induced holidays per test sample.

TABLE I

| Test Pipe Sample Data | | | | |
|---|---|---|---|---|
| Test Pipe Sample # | Days in Test | Disbonded AREA ASTM G-8 (cm²) | Disbonded AREA DLC (cm²) | Capacitance Microfarads |
| 1 | 30 | 6.2 | 6.3 | 1260 |
| 2 | 60 | 7.4 | 14.7 | 2934 |
| 3 | 60 | 8.1 | 8.8 | 1765 |
| 4 | 30 | 11.4 | 11.7 | 2329 |
| 5 | 30 | 16.2 | 16.2 | 3245 |

FIG. 6 is a graph chart depicting double layer capacitance (DLC) as a function of time.

The change in the double layer capacitance (DLC) of the five test pipe samples shown above with time is shown graphically in FIG. 6.

It is also important to note that these test data can be used to determine the long term behavior of an anti-corrosion protective coating to cathodic potentials. For example, sample curves 2 and 3 in FIG. 6, show an initial increase in double layer capacitance (DLC) within the first 20 days, and then virtually no change. On the other hand, sample curves 4 and 5 in FIG. 6, show steadily increasing double layer capacitance (DLC), for at least up to 30 days.

Table I indicates a very good correlation between the electronically measured cathodically disbonded area, and the disbonded area as determined by the prior art destructive method. In sample #2 in Table I, a larger disbonded area is indicated by the electronic method, which is likely accounted for by an unintentional holiday in the test pipe specimen. In a few other samples, a smaller disbonded area was indicated by the double layer capacitance (DLC) method. This discrepancy is most likely due to the inability to distinguish, when using the prior art destructive method, between poor interface adhesive bonding, (which may not allow entrance of the electrolyte) and cathodic disbonding.

The instant invention technique of double layer capacitance (DLC) measurements for the determination of the extent of in-situ cathodic disbondment areas on wrapped pipe samples, provides a test method that is at once useful as a non-destructive test, that will provide precise information of the extent of the area of cathodic disbondment vs. time, and provides less subjective results, than the destructive method currently in use.

The previous detailed description of the preferred embodiment of the present invention is given for purposes of clarity of understanding only, and no unnecessary limitations should be understood or implied therefrom, as such functions and equivalents may be obvious to those skilled in the art pertaining thereto.

What is claimed is:

1. A method of evaluating the corrosion protection afforded to a metallic surface by a surface coating thereon, by measuring the extent of cathodic disbondment, wherein said metallic surface is contacted by an electrolyte fluid, comprising the steps of:

establishing and equilibrating a circuit path through a working test pipe electrode and a counter electrode in said electrolyte fluid, in which said test pipe electrode achieves a state of cathodic protection;

disconnecting said cathodically protected working test pipe electrode from said counter electrode;

re-establishing a circuit path through said working test pipe electrode, said counter electrode, and a reference electrode, in said electrolyte fluid, along with an electronic control and measuring means;

causing a measured known voltage step to be applied to said working test pipe electrode;

measuring the current flowing after application of said measured applied voltage step; and analyzing said current flow data and thereby determining the double layer capacitance at the interface between said working test pipe electrode and said electrolyte fluid.

2. A method of evaluating corrosion protection according to claim 1, wherein said current flow data is being continuously monitored and recorded.

3. A method of evaluating corrosion protection, according to claim 1, wherein a predetermined program stored in a microcomputer controller provides operational signals to said electronic control and measuring means.

4. A method of evaluating corrosion protection, according to claim 1, wherein said voltage step applied to said test pipe electrode is in the range of from about 10 to 300 mv.

5. A method of evaluating corrosion protection, according to claim 1, wherein said counter electrode is made of magnesium.

6. A method of evaluating corrosion protection, according to claim 1, wherein said reference electrode is a calomel electrode.

7. A method of evaluating corrosion protection, according to claim 1, wherein said double layer capacitance is measured for said test pipe electrode as a function of pipe potential vs. said reference electrode.

8. A method of evaluating corrosion protection according to claim 1, wherein said electronic control and measuring means comprises a microcomputer controller, a scanner, a potentiostat, a voltmeter, and a plotter in working relationship with each other.

* * * * *